United States Patent [19]

Heaton et al.

[11] Patent Number: 5,276,264
[45] Date of Patent: Jan. 4, 1994

[54] SUNFLOWER PRODUCTS HAVING LOWER LEVELS OF SATURATED FATTY ACIDS

[75] Inventors: Thomas C. Heaton, Davis; Glenn S. Cole, Woodland, both of Calif.; Barry A. Martin, Urbandale, Iowa

[73] Assignee: Pioneer Hi-Bred International, Inc., Des Moines, Iowa

[21] Appl. No.: 810,664

[22] Filed: Dec. 19, 1991

Related U.S. Application Data

[63] Continuation-in-part of Ser. No. 638,941, Jan. 9, 1991, abandoned.

[51] Int. Cl.$^5$ .................. A01H 1/02; A01H 5/10; A01H 1/00
[52] U.S. Cl. .................. 800/200; 800/255; 800/DIG. 14; 800/DIG. 69; 47/58
[58] Field of Search .................. 800/200, 255, DIG.; 47/58, 58.04

[56] References Cited

U.S. PATENT DOCUMENTS

4,627,192  12/1986  Fick .................. 47/58

OTHER PUBLICATIONS

Food Fats and Health, R118, Dec. 1991, 96 pp., Council for Agricultural Science and Technology, Ames, Iowa.
Giorio, G., F. Sunseri, and F. Montemurro, 1991, Preliminary evidence of the gentic control of oleic acid content in a cross between sunflower line, Abs. BR09, Sunflower Biotechnology in Europe, Mittelwihr, France, Sep. 3–6, 1991, p. 10.
Riegger, R., A. Michaelis, and M. M. Green, 1976, Glossary of Genetics and Cytogentics, Classical and Molecular, 4th Edition Springer-Verlag, New York, 647 pp.
Mayo, O., 1980, The Theory of Plant Breeding, Oxford University Press, New York, 293 pp.
Leclerg, P. 1969, Une sterilite male cytoplasmique chez le tournesol. Ann. Amelior. Plantes. 19:99–106, (English Summary).
Whelan, E. D. P., and W. Dedio, 1980, Registration of sunflower composite crosses with CMC1, CMG2, and CMG3, Crop. Sci. 20:832.
Heiser, C. B. 1982, Registration of Indiana-1 CMS sunflower germplasm. Crop Sci. p. 1089.
Skoric, D. 1988, Development of Sunflower hybrids on the basis of cytoplasmic sterility, Journal of Edible Oil Industry, Jul. 1988 pp. 54–70.
Urie, A. L., 1985, Inheritance of high oleic acid in sunflower, Crop. Sci. 25:986–989.
Brigham, R. D. 1990, Sunflower (Helianthus annus L.) lines and germplasms released in Texas and the USA, 1964–1988, MP-1684, Jun. 1990, Texas Agricultural Experiment Station, The Texas A&M University System, College Station, Tex. 7 pp.
Ivanov, P., D. Petakov, V. Nikolova, and E. Pentchev, 1988 Sunflower breeding for high palmitic acid content in the oil. Proc. of the 12th Int. Sunflower Conf. vol. 2 Novi Sad, Yugoslavia Jul. 25–29, 1988, pp. 463–465.
Kohler, R. H., R. Horn, A. Lussi, and K. Zetsche, 1991, Cytoplasmic male sterility in sunflower is corrolated with the co-transcription of a new open reading frame with the aptA gene. Mol. Gen. Genet. 227:369–376.
Erickson, E. A., J. R. Wilcox, and J. F. Cavins, 1988, Fatty Acid Composition of the Oil in Reciprocal Crosses among Soybean Mutants, Crop Sci. 28:644–646.
Fick, G. N. 1984, Inheritance of high oleic acid in the seed oil of sunflower, p. 9, Proc. Sunflower Research Workshop, Bismark, N. D. 1 Feb., National Sunflower Association, Bismark, N.D.
Soldatov, K. 1976, Proc. 7th Int. Sunfl. Conf., ISA: Vlaardingen, The Netherlands, pp. 352–357.
Downey et al. 1971, Proc. Flax Inst. USA 41:1–3.
Garces et al. 1989, Phytochemistry 28(10):2593–5.
Knowles, P. 1988, Proc. World Conf. Biotechnol. Fats Oils Ind., AOCS: Champaign, Ill., pp. 35–38.
Ram et al. 1988, Proc. World Conf. Biotechnol. Fats Oils Ind.; AOCS: Champaign, Ill., pp. 65–71 Miller et al. 1987, Crop Sci. 27:923–926.

*Primary Examiner*—David T. Fox
*Attorney, Agent, or Firm*—Nina L. Pearlmutter; Michael J. Roth

[57] ABSTRACT

Sunflower seed, plants and oil are described which have a total level of saturated fatty acids equal to 6% or less relative to the total fatty acid content, a total level of stearic acid less than 1% of the total fatty acid content, and a total level of palmitic acid less than 3% of the total fatty acid content.

10 Claims, No Drawings

SUNFLOWER PRODUCTS HAVING LOWER LEVELS OF SATURATED FATTY ACIDS

REFERENCE TO PRIOR COPENDING APPLICATION

This is a continuation-in-part of prior copending application Ser. No. 07/638,941 filed Jan. 9, 1991 now abandoned.

BACKGROUND OF THE INVENTION

This invention relates to a novel sunflower (Helianthus spp.) plant, to products obtained from the novel plant and to methods of producing the sunflower products.

The cultivated sunflower (*Helianthus annuus* L.) is a major worldwide source of vegetable oil. In the United States, approximately 4 million acres are planted in sunflowers annually, primarily in the Dakotas and Minnesota.

The very rapid expansion over the last decade of acreage planted in sunflower in the United States is due in part to several important developments in the field of sunflower breeding and varietal improvement. One significant development was the discovery of cytoplasmic male sterility and genes for fertility restoration, a discovery that allowed the production of hybrid sunflowers. The hybrids thus produced were introduced during the early 1970's.

A description of cytoplasmic male sterility (CMS) and genetic fertility restoration in sunflowers is presented by Fick, "Breeding and Genetics," in *Sunflower Science and Technology* 279-338 (J. F. Carter ed. 1978), the contents of which are incorporated herein by reference.

Sunflower oil is comprised primarily of palmitic, stearic, oleic, linoleic and linolenic acids. While other unusual fatty acids exist in plants, palmitic, stearic, oleic, linoleic, and linolenic acids comprise about 88% of the fatty acids present in the world production of vegetable oils. (Harwood, J. L., Plant Acyl Lipids: Structure, Distribution and Analysis, 4 *Lipids: Structure and Function,* P. K. Stumpf and E. E. Conn ed. (1988)). Palmitic and stearic acids are saturated fatty acids that have been demonstrated in certain studies to contribute to an increase in the plasma cholesterol level, a factor in coronary heart disease. Vegetable oils high in unsaturated fatty acids, such as oleic and linoleic acids, may have the ability to lower plasma cholesterol according to recent studies. Saturated fatty acids also have higher melting points in general than unsaturated fatty acids of the same carbon number, which contributes to cold tolerance problems in foodstuffs and can contribute to a waxy or greasy mouthfeel. It is also known that food products made from fats and oils having less than about 3% saturated fatty acids will typically contain less than 0.5 gram saturated fat per serving and as a result can be labeled as containing "zero saturated fat" under current labeling regulations. Thus, for a number of reasons it is desirable to produce a sunflower oil having low levels of palmitic and stearic acids and high levels of oleic or linoleic acids.

Prior to the present invention there were no naturally occurring sources of low saturated fatty acid sunflower oils. The generally accepted pathway of fatty acid biosynthesis in plants is that palmitic and stearic acids are the products of the beta ketoacyl-ACP synthetase system which includes three isozymes which are referred to as KAS I, II and III. Stearoyl-ACP acid is desaturated to oleic acid which is esterified to phosphatidylcholine then sequentially desaturated to linoleic and linolenic acids (Stymne, S. and Stobart, A. K., Triacylglycerol Biosynthesis, 9 *The Biochemistry of Plants: A Comprehensive Treatise* 175-214 (1987) and Stumpf, P. K., Biosynthesis of Fatty Acids in Higher Plants, *Oil Crops of the World* 38-62 (1989). Previously published research in sunflower has emphasized generally the alteration of the percentage of oleic or linoleic acids. The relative proportions of oleic and linoleic acids can be environmentally influenced (Kinman, M. L., and F. R. Earle., "Agronomic Performance and Chemical Composition of the Seed of Sunflower Hybrids and Introduced Varieties," *Crop Science* 4:417-420 (1964); Putt, E. D., B. M. Craig, and R. B. Carson. "Variation in Composition of Sunflower Oil from Composite Samples and Single Seeds of Varieties and Inbred Lines, *J. Am. Oil Chem. Soc.* 46:126-129 (1969); Seiler, G. J., "Variation in Oil and Oil Quality of Wild Annual Sunflower (*Helianthus annuus* L.) Populations in a Uniform Environment," 10*th International Sunflower Conference,* Mar. 14-18, 1982. Surfers' Paradise, Australia. p. 212-215; Seiler, G. J., "Effect of Genotype, Flowering Date, and Environment on Oil Content and Oil Quality of Wild Sunflower Seed," *Crop Science,* 23: 1063-1068 (1983); Seiler, G. J., "Interrelation of Fatty Acids in Oil of Wild Annual Sunflower (*Helianthus annuus* L.)" *Proceedings of the XI International Sunflower Conference.* Mar. 10-13, 1985. Mar del Plata, Argentina. p. 529-534; or have been shown in certain genotypes to be inherited in stable manner (Soldatov, K. I., "Chemical Mutagenesis in Sunflower Breeding," *International Proceedings, 7th International Sunflower Conference,* Krasnodar, U.S.S.R., 27 June-3 July, 1976. International Sunflower Association Vlaardingen, p. 352-357, The Netherlands; Karachenko, L. N., "Genotypic and Phenotypic Mechanisms Ensuring Regulation of Fatty Acid Biosynthesis in Sunflower Seeds," *Fiziologiya Rastenii* (Russian) 26: 1226-1232 (1979); Fick, G. N., "Breeding and Genetics," *Sunflower Science and Technology,* Carter, Jack F. (ed.). 1978. Urie, A. L., "Inheritance of Very High Oleic Acid Content in Sunflower," *Proc. Sunflower Research Workshop.* Bismarck, N.D. 1 February, 1984. National Sunflower Association. Bismarck, N.D. p.9-10; Miller, J. F. and D. C. Zimmerman. "Inheritance of High Oleic Fatty Acid Content in Sunflower." *Proc. Sunflower Research Workshop.* Fargo, N.D. 26 January, 1983. National Sunflower Association. Bismarck, N.D. p. 10; Urie, A. L., "Inheritance of High Oleic Acid in Sunflower." *Crop Science* 25:986-989 (1985); Simpson, B. W. and D. L. George, "Potential for Selection of Fatty Acids on a Single Seed Basis in Sunflower (*Helianthus annuus* L.)." *Proceedings of the XI International Sunflower Conference,* Mar. 10-13, 1985. Mar del Plata, Argentina. p 791-796; Miller, J. F., D. C. Zimmerman, and B. A. Vick, "Genetic Control of High Oleic Acid Content in Sunflower Oil," *Crop Science* 27:923-926 (1987); George, D. L., B. W. Simpson, and C. M. McLeod. "Proposed Development of a High Linoleic Acid Sunflower Hybrid." *Proceedings of the 12th International Sunflower Conference.* Jul. 25-29, 1988. Novi Sad, Yugoslavia. p 448-453; Simpson, B. W., C. M. McLeod and D. L. George. "Selections for High Linoleic Acid Content in Sunflower (*Helianthus annuus* L.)." *Aust. J. of Exper. Agric.* 29:233-239 (1989). Recent research has claimed that the level of palmitic acid in sunflower oil can be increased to as high as 40.2% of the total oil (Ivanov, P, D. Petakov, V. Nikolova, and E. Pentchev, "Sunflower Breeding for High Palmitic Acid Content in the Oil." *Proceedings of the 12th International Sunflower Conference.* Vol II. Jul. 25-29, 1988. Novi Sad, Yugoslavia. p 463-465). The invention disclosed here pertains to the proportion of palmitic and stearic acids relative to the other major fatty acids in sunflower oil: oleic and linoleic acids.

SUMMARY OF THE INVENTION

It is an object of the present invention to provide a sunflower seed that has a total saturated fatty acid content of approximately 6% or less.

It is another object of the present invention to provide a new sunflower which is true-breeding under a wide variety of growing conditions for the trait of low saturated fatty acid content. This trait can be identified and characterized by restriction fragment length polymorphism analysis of the genome of the sunflower varieties provided by this invention.

It is a further object of the present invention to provide new sunflower plants that can be used efficiently to produce parent lines and hybrids possessing desirable agronomic traits in combination with a low content of saturated fatty acids.

It is yet another object of the present invention to provide a method for producing a hybrid sunflower that has seed which has a total saturated fatty acid content of approximately 6% or less.

It is still another object of the present invention to provide a novel sunflower oil that has a total level of saturated fatty acids of 6% or less.

In accomplishing the foregoing objects, there has been provided, in accordance with the present invention, a sunflower seed having a total saturated fatty acid content of 6% or less.

There has also been provided, in accordance with another aspect of the present invention, a hybrid sunflower which is cytoplasmic male sterile, or alternatively, which comprises a genetic determinant encoding fertility restoration, and which, in addition, produces seed the triglycerides of which have a total saturated fatty acid content of 6% or less.

In accordance with yet another aspect of the present invention, there has been provided a sunflower oil which as obtained from the sunflower seed contains approximately 6% total saturated fatty acids or less relative to its total fatty acid content.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

In the description and examples that follow, a number of terms are used herein. In order to provide a clear and consistent understanding of the specification and claims, including the scope to be given such terms, the following definitions are provided:

Sunflower Seed: Botanically referred to as an "achene", comprised of the pericarp and embryo.

Maintainer Line: A male fertile version of an inbred sunflower line.

Cytoplasmic male sterile (CMS) plant or inbred line: A sunflower line that produces no viable pollen is called male sterile. Male sterility is inherited maternally, i.e. the male sterile plant is used as the female parent in a cross with pollen from another sunflower. CMS lines are produced by crossing a maintainer line with a sunflower plant with the cytoplasmic male sterility trait and then backcrossing to the maintainer line until a male sterile line that is homologous to the maintainer line in all other respects is developed. CMS lines are also referred to as female lines.

Restorer Line: A line possessing the gene or genes to restore male fertility or viable pollen to a sunflower hybrid or inbred line and progeny having a maternal cytoplasm that conditions male sterility. This term is also discussed in the literature. See, for example, the Fick article identified above.

Plant Breeding

To produce the novel sunflower of the present invention sunflower line VK9G was emasculated and crossed with pollen of variety 'Pervenets.' Inbred line VK9G is a male fertile sunflower line that produces seeds which have a normal fatty acid composition. 'Pervenets' is an open-pollinated (heterogenous) variety introduced from the USSR in the 1970's (Soldatov, 1976) with high levels of oleic acid. Similiar breeding methods are described in Fernandez-Martinez, J., Dominguez-Gimenez, J. and Jimenez-Ramirez, A., Breeding for High Content of Oleic Acid in Sunflower (*Helianthus annuus* L.) Oil, *Helia Nr. Scientific Bulletin of the F.A.O. Research Network on Sunflower* 11-15 (1988); Fick, G. N., Sunflower, *Oil Crops of the World* Ch. 14 pp 301-318 (1989); Knowles, P. F. Genetics and Breeding of Oil Crops, *Oil Crops of the World* Ch. 12 pp 260-282 (1989). Pedigree selection was made for six generations. A fatty acid analysis was done on the seeds of maintainer lines that had been inbred for six generations ($F^6$) from the pedigree VK9GXPervenets. Also the CMS counterparts of the maintainer lines were analyzed for fatty acid composition. At that time, the maintainer lines had been backcrossed into the CMS background three times so the CMS counterpart was 87.5% homologous to the maintainer lines.

Breeding with the lines was continued in Hawaii by self pollinating heads (capitulae) of the maintainer lines and crossing pollen from individual heads of the maintainer lines to their respective sterile counterparts so the identity of each crossed pair was preserved. Fatty acid analyses were done on seeds of the maintainer lines and selected seeds were planted again in Woodland, CA. Crosses between the maintainer line and the male sterile counterpart were made in pairs and selections were made for good agronomic plant traits. Fatty acid analysis were performed on a bulk of five seeds from each pair of maintainer and sterile lines derived from that cross. The maintainer selections were (VK9G/PERV)XC111211 and (VK9G/PERV)XC111121. Those lines were the $F_7$ generation of inbreeding and were referred to as 8904W04G and 8904W06G. The male sterile counterpart was greater than 97% homologous to its respective maintainer, having been crossed 5 times. At that time it was noted for the first time that the seed from the male sterile form of each maintainer had lower total saturated fatty acids than the maintainer. The results of this analysis are shown in Table 1.

TABLE 1

| Entry | Name | Source | Unsaturates | | Saturates | |
|---|---|---|---|---|---|---|
| | | | % 18:2 | % 18:1 | % 16:0 | % 18:0 |
| 28 | 8904W04F | 8WB9-3 4-1 | 4.0 | 89.9 | 3.9 | 2.2 |
| 29 | 8904W04G | 8WB9-4 4-1 | 3.9 | 86.2 | 3.5 | 6.4 |
| 32 | 8904W06F | 8WB9-3 6-1 | 3.7 | 90.4 | 2.0 | 1.9 |
| 33 | 8904W06G | 8WB9-4 6-1 | 3.2 | 86.6 | 2.2 | 5.9 |

Pairs of sterile and maintainer sister lines from the Woodland nursery were sent to Kekaha, Hi. for winter nursery breeding. Additional pairs of maintainer and CMS counterparts were crossed Seeds from those crosses were analyzed. Once again the sterile forms of the maintainer lines had lower total saturated fatty acids. Saturated fatty acids of the sterile lines comprised less than 7% of the total oil content. Maintainer line selections of 8904W03G (a sister line selection of 8904W05G and 8904W06G) and 8904W06G had total saturated fatty acid amounts between 8.3 and 10.2% of the total oil content which was higher than their sterile counterparts (Table 2.).

The fact that total saturated fatty acids in the sterile forms were less than that of the corresponding maintainers in the Hawaii test as well as at the Woodland test demonstrated that a nucleo-cytoplasmic interaction in those lines affected fatty acid synthesis. Specifically, there was a demonstrated cytoplasmic influence on fatty acid synthesis such that the total stearic and palmitic acid content is less in seed of the sterile form (F) than in the paired maintainer line (G). The result is less total saturated fatty acids in the sterile line. This trait is inherited from generation to generation across different environments demonstrating that low total content of saturated fatty acids in these sunflower lines is genetically determined in a predictable and heritable manner.

TABLE 2

| Entry | Name | Source | Unsaturates % | | | Saturates % | |
|---|---|---|---|---|---|---|---|
| | | | 18:2 | 18:3 | 18:1 | 16:0 | 18:0 |
| 60 | 8904W03F | L8-91811k1 | 4.3 | 0.6 | 88.1 | 4.8 | 2.2 |
| 61 | 8904W03G | L8-92811k1 | 3.0 | 0.6 | 87.9 | 3.5 | 5.0 |
| 62 | 8904W03F | L8-91811k2 | 4.2 | 0.5 | 88.6 | 4.9 | 1.8 |
| 63 | 8904W03G | L8-92811k2 | 2.9 | 0.6 | 88.2 | 3.8 | 4.5 |
| 64 | 8904W03F | L8-91811k3 | 4.6 | 0.5 | 88.1 | 4.9 | 2.0 |
| 65 | 8904W03G | L8-92811k3 | 3.0 | 0.6 | 87.4 | 3.7 | 5.3 |
| 66 | 8904W06F | L8-91812k1 | 0.2 | 0.2 | 88.9 | 4.6 | 2.1 |
| 67 | 8904W06G | L8-92812k1 | 0.4 | 0.1 | 86.1 | 3.8 | 6.9 |
| 68 | 8904W06F | L8-91812k3 | 4.0 | 1.4 | 88.1 | 4.4 | 2.1 |
| 69 | 8904W06G | L8-92812k3 | 3.2 | 0.3 | 80.7 | 5.1 | 5.1 |

In the Woodland nursery, the sterile counterparts of 8904W03G and 8904W06G were crossed with restorer lines. That hybrid seed was distributed to sunflower research stations for testing in California, France, and Argentina. Hybrids were grown, and bags were placed on heads prior to flowering to force self pollination of the hybrid and prevent contamination. Seeds from individual heads of those hybrids were analyzed for fatty acid composition. It was found that oil in bulked seeds of individual heads from hybrids made with the female (male sterile) inbreds 89W04W03F and 89W04W06F was low in total saturated fatty acids (Table 3.). The fact that individual heads had seeds whose oil in a bulk sample had low levels of saturated fatty acid demonstrated that such levels can be produced in a hybrid as well as parental inbred lines. Moreover, the low total saturates were obtained in three different sunflower growing environments. It was demonstrated that these male sterile lines when used as female parents produced low saturated fatty acids in hybrids grown in typical sunflower crop production areas.

TABLE 3

Results of fatty acid analyses of composite seed samples from individual self pollinated heads from hybrids made using 8904W06F and 8904W03F as the female parent grown in three environments.

| Location | Hybrid | Head | Sterile | Unsaturates % | | Saturates % | |
|---|---|---|---|---|---|---|---|
| | | | | 18:2 | 18:1 | 16:0 | 18:0 |
| Montech, France | 8W1070 | Bulk | 8904W06F | 2.1 | 94.1 | 2.8 | 1.0 |
| Woodland, California | 8W1070 | 1 | 8904W06F | 4.4 | 87.6 | 5.4 | 2.3 |
| | | 2 | | 4.2 | 89.5 | 5.3 | 1.1 |
| | | 3 | | 4.5 | 91.1 | 3.5 | 0.9 |
| | | 4 | | 7.0 | 88.2 | 3.6 | 1.2 |
| | | 5 | | 3.8 | 90.8 | 4.5 | 0.9 |
| | 8W1075 | 1 | 8904W03F | 3.5 | 91.6 | 3.9 | 1.0 |
| | | 2 | | 8.6 | 86.4 | 3.7 | 1.3 |
| | | 3 | | 4.0 | 90.6 | 4.4 | 0.9 |
| | | 4 | | 4.0 | 91.0 | 4.2 | 0.9 |
| Venado Tuerto, Argentina | 8W1070 | 1 | 8904W06F | 10.4 | 80.0 | 4.1 | 5.1 |
| | | 2 | | 1.7 | 91.4 | 3.8 | 3.1 |
| | | 3 | | 1.6 | 93.5 | 3.3 | 1.5 |
| | | 4 | | 1.9 | 93.6 | 3.7 | 0.7 |
| | 8W1075 | 1 | 8904W03F | 1.9 | 92.8 | 3.6 | 1.7 |
| | | 2 | | 1.7 | 94.2 | 3.2 | 0.9 |
| | | 3 | | 2.2 | 93.4 | 3.4 | 1.0 |
| | | 4 | | 2.3 | 93.5 | 3.4 | 1.0 |
| 6440 Standard Comparison | | | | 66.2 | 20.8 | 7.0 | 5.8 |

Data from other fatty acid analyses of sunflower seed were reviewed. A number of restorer lines were found that had total saturated fatty acid levels of less than 5% (Table 4).

TABLE 4
Summary of restorer lines found in fatty acid analysis screening that have less than 5% total saturated fatty acid levels.

| Line | Selection | % 16:0 | % 18:0 | Total Sat | % 18:1 | % 18:2 |
|---|---|---|---|---|---|---|
| 9A4W005M | 1 | 3.0 | 1.6 | 4.6 | 90.8 | 4.5 |
| 9A4W005M | 6 | 3.2 | 1.4 | 4.6 | 91.4 | 4.0 |
| 9A4W005M | 7 | 3.2 | 1.6 | 4.8 | 94.9 | 2.0 |
| 9A4W005M | 11 | 3.1 | 1.5 | 4.6 | 91.7 | 3.8 |
| 9B3W006M | 1 | 2.8 | 1.8 | 4.6 | 92.7 | 2.7 |
| 9B3W006M | 3 | 2.9 | 2.0 | 4.9 | 93.2 | 1.8 |
| 9B3W006M | 11 | 2.6 | 1.0 | 3.6 | 94.4 | 1.9 |
| 9B3W006M | 12 | 3.2 | 1.5 | 4.7 | 92.4 | 2.8 |
| 9E-RUN737 | 2 | 2.3 | 1.8 | 4.1 | 95.0 | 1.0 |

In the Hawaiian winter nursery hybrids were synthesized by crossing female sunflower lines having seeds with less than 6% total saturated fatty acids with male (restorer) lines having seed with less than 6% total saturated fatty acids. Seeds from the plants resulting from those crosses were planted at Woodland, Calif. and Moorhead, Minn. At flowering, heads of those hybrids were bagged to assure self pollination. Heads were harvested and individual seeds from separate identity preserved heads were analyzed for fatty acid composition. The results are presented in Table 5.

TABLE 5
Summary of total saturated fatty acid (SFA) levels in seeds of individual self pollinated heads of hybrids grown in Woodland, CA and Moorhead, MN.

| Hybrid | Location | Heads no. | Seeds no. | SFA % mean | Lowest SFA % Observation single | seedsingle head |
|---|---|---|---|---|---|---|
| 9W1204 | Moorhead | 5 | 25 | 4.8 | 3.9 | 4.1 |
|  | Woodland | 5 | 25 | 5.2 | 4.0 | 4.3 |
| 9W1224 | Moorhead | 5 | 25 | 4.5 | 4.0 | 4.2 |
|  | Woodland | 5 | 25 | 5.3 | 4.5 | 4.8 |
| 9W1234 | Moorhead | 5 | 25 | 4.6 | 3.8 | 4.2 |
|  | Woodland | 5 | 23 | 5.6 | 4.8 | 5.2 |
| 9W1244 | Moorhead | 3 | 15 | 4.4 | 4.0 | 4.1 |
|  | Woodland | 5 | 25 | 5.4 | 4.3 | 5.1 |
| 9W1284 | Moorhead | 5 | 25 | 4.7 | 4.4 | 4.6 |
|  | Woodland | 5 | 24 | 5.9 | 3.9 | 4.8 |
| 6440 | Moorhead | 5 | 25 | 10.4 | 9.0 | 9.8 |
| Standard | Woodland | 5 | 25 | 10.5 | 8.8 | 10.5 |

The data in Table 5 demonstrate that inbred sunflower lines having less than 6% total saturated fatty acids combined to produce hybrids whose seed had less than 6% total saturated fatty acids in both the Woodland and Moorhead environments. Individual heads were produced in both environments that had less than 5% total saturated fatty acids. In both environments individual seeds were also produced that had less than 4% total saturated fatty acids.

In order to validate the maternal cytoplasmic effect on the level of saturated fatty acids in this discovery, female line 8904W06F with cytoplasm conferring low saturated fatty acid totals was crossed with another sunflower maintainer line PHA078. PHA078 is a proprietary inbred line having high oleic acid content. As expected, the progeny from the cross of 8904W06F/PHA078 were sterile hybrids since PHA078 is a maintainer line and lacks genes for male fertility restoration of 8904W06F. These male sterile plants were crossed with pollen from three other lines: PHA076, 9B3W006M, and PHA061. PHA076 and 9B3W006M are inbred lines having high oleic acid content. PHA061 is an inbred line with normal fatty acid composition. As a result of this cross, each seed from plants of 8904W06F/PHA078 could be classified as having the cytoplasm of 8904W06F and a nuclear genotype which is contributed ¼ by 8904W06F, ¼ PHA078, and ½ PHA076, 9B3W006M, or PHA061. These seeds were analyzed for fatty acid composition. The data are presented in Table 6.

TABLE 6
Summary of total saturated fatty acid levels (SFA %) in seeds with cytoplasmic background conferring low saturated fatty acid traits with nuclear parentage 75% distinct from 8904W06F.

| Cross | Seeds no. | SFA % mean | % Fatty Acids Composition | | | |
|---|---|---|---|---|---|---|
| | | | 16:0 | 18:0 | 18:1 | 18:2 |
| 8904W06F*PHA078/PHA076 | 10 | 3.80 | 2.91 | 0.89 | 93.78 | 2.77 |
| Lowest SFA of cross | 1 | 3.30 | 2.70 | 0.60 | 94.40 | 2.30 |
| 8904W06F*PHA078/9B3W006M | 10 | 3.97 | 3.10 | 0.87 | 94.09 | 1.91 |
| Lowest SFA of cross | 1 | 3.40 | 2.70 | 0.70 | 95.30 | 1.40 |
| 8904W06F*PHA078/PHA061 | 10 | 4.03 | 3.07 | 0.96 | 91.46 | 4.47 |
| Lowest SFA of cross | 1 | 3.40 | 2.50 | 0.90 | 93.90 | 2.70 |

The data from Table 6 demonstrate that even when the nuclear component of 8904W06F is diluted to 75% by four other lines (PHA078, PHA076, 9B3W006M, and PHA061) having either normal oil composition or higher oleic fatty acid composition, the cytoplasmic effect caused by the maternal parent 8904W06F is maternally transmitted and the progeny have seeds with lower total saturated fatty acid content.

Thus, while not intending to be limited by theory, it appears that the cytoplasm contains the factors which control for reduced saturated fatty acid levels. These cytoplasmic factors can be transferred to offspring when the plants according to this invention are used as the female parent in a cross with other sunflower cultivars, providing a method of reducing the content of saturated fatty acid moieties in any sunflower cultivar by conventional crossing and backcrossing.

Applicants have made available to the public without restriction a deposit of at least 2500 seeds of a sunflower designated 8904W03F with the American Type Culture Collection (ATCC), Rockville, Md. 20852, U.S.A. The seeds deposited with the ATCC are taken from the same deposit maintained by Pioneer Hi-Bred International, Inc., 700 Capital Square, 400 Locust Street, Des Moines, Iowa 50309, since prior to the filing date of this application. The deposit will be maintained without restrictions, at the ATCC Depository, which is a public depository, for a period of 30 years, or five years after the most recent request, or for the effective life of the patent, whichever is longer, and will be replaced if it becomes nonviable during that period.

What is claimed is:

1. A sunflower plant that is the product of crossing a male parental line and a female parental line, and that has a trait inherited cytoplasmically from sunflower line 8904W03F or a plant derived from sunflower line 8904W03F such that said sunflower plant, when subjected to forced self-pollination, yields bulked seed from individual heads thereof that provides oil comprising stearic acid in an amount lower than the stearic acid content characterizing a sunflower line that has the nuclear genotype of said female parental line but that lacks said trait.

2. A sunflower plant of claim 1, wherein said oil has a stearic acid content that is on the order of 50% to 88% lower than said stearic acid content characterizing said male parental line.

3. A sunflower plant of claim 1, wherein said oil is characterized by a percentage of total stearic acid that is about 0.7% to 2.3%.

4. A sunflower plant of claim 1, wherein said sunflower plant is an inbred.

5. A sunflower plant that is cytoplasmically male-sterile and that has a trait inherited cytoplasmically from sunflower line 8904W03F or a plant derived from sunflower line 8904W03F such that said sunflower plant, when pollinated with pollen of a maintainer line, yields bulked seed from individual heads thereof that provides oil comprising stearic acid in an amount lower than the stearic acid content characterizing said maintainer line.

6. A seed of sunflower plant according to claim 1.

7. A seed of sunflower plant according to claim 4.

8. A seed of sunflower plant according to claim 5.

9. A hybrid sunflower plant that is the product of a cross wherein a sunflower plant of claim 1 is the female parent, wherein said hybrid has said trait such that, when it is subjected to forced self-pollination, said hybrid yields bulked seed from individual heads thereof that provides oil comprising stearic acid in an amount lower than the stearic acid content characterizing a sunflower line that has the nuclear genotype of said female parental line but that lacks said trait.

10. A seed of sunflower plant according to claim 9.

* * * * *

UNITED STATES PATENT AND TRADEMARK OFFICE
CERTIFICATE OF CORRECTION

PATENT NO. : 5,276,264
DATED : January 4, 1994
INVENTOR(S) : Thomas C. Heaton, Glenn S. Cole, Barry A. Martin It is certified that error appears in the above-indentified patent and that said Letters Patent is hereby corrected as shown below:

column 8, line 44 after "U.S.A." please insert --, as ATCC Deposit Number 75180, deposited on January 9, 1992.--.

Signed and Sealed this

Eighteenth Day of October, 1994

Attest:

BRUCE LEHMAN

*Attesting Officer*  *Commissioner of Patents and Trademarks*